(12) United States Patent
Lang et al.

(10) Patent No.: US 6,422,867 B2
(45) Date of Patent: Jul. 23, 2002

(54) INTERPROXIMAL FLOSSER HANDLE

(75) Inventors: Kenneth J. Lang, Loveland; Lynne M. Calliott; Brian R. Williams, both of Fort Collins; Theodore De Leo, Loveland; William B. Stephens, Boulder, all of CO (US)

(73) Assignee: Water Pik, Inc., Fort Collins, CO (US)

( * ) Notice: Subject to any disclaimer, the term of this patent is extended or adjusted under 35 U.S.C. 154(b) by 0 days.

(21) Appl. No.: 09/746,598

(22) Filed: Dec. 20, 2000

Related U.S. Application Data

(60) Provisional application No. 60/171,825, filed on Dec. 21, 1999.

(51) Int. Cl.$^7$ .................................................. A61C 1/07
(52) U.S. Cl. ....................................... 433/118; 132/322
(58) Field of Search ................................ 433/118, 116, 433/119, 142, 143, 147, 82, 125; 132/322

(56) References Cited

U.S. PATENT DOCUMENTS

| | | | |
|---|---|---|---|
| 684,951 A | * 10/1901 | Rothkranz | .................. 433/116 |
| 1,355,037 A | 10/1920 | Dziuk | |
| 1,703,642 A | 2/1929 | Sticht | |
| 2,016,597 A | 10/1935 | Drake | |
| 2,931,371 A | 4/1960 | Petitta | |
| 3,106,216 A | 10/1963 | Kirby | |
| 3,270,416 A | 9/1966 | Massa | |
| 3,335,443 A | 8/1967 | Parisi et al. | |
| 3,375,820 A | 4/1968 | Kuris et al. | |
| 3,472,045 A | 10/1969 | Nelsen et al. | |
| 3,472,247 A | 10/1969 | Borsum et al. | |
| 3,474,799 A | 10/1969 | Cappello | |
| 3,552,022 A | 1/1971 | Axelsson | |
| 3,559,292 A | 2/1971 | Weissman | |
| 3,563,233 A | 2/1971 | Bodine | |
| 3,588,936 A | 6/1971 | Duve | |
| 3,660,902 A | 5/1972 | Axelsson | |
| 3,672,378 A | 6/1972 | Silverman | |
| 3,759,274 A | 9/1973 | Warner | |

(List continued on next page.)

FOREIGN PATENT DOCUMENTS

| | | |
|---|---|---|
| DE | 243224 | 4/1910 |
| DE | 17 66 651 C1 | 12/1981 |
| DE | 3431481 | 2/1986 |
| DE | 8626725 | 5/1987 |
| DE | 37 36 308 A1 | 7/1989 |
| DE | 41 42 404 C2 | 7/1991 |
| DE | 42 23 195 A1 | 1/1994 |
| DE | 42 23 196 A1 | 1/1994 |
| DE | 42 26 659 A1 | 2/1994 |
| DE | 43 09 078 A1 | 9/1994 |
| DE | 297 15 234 U1 | 12/1997 |
| EP | 0 354 352 | 2/1990 |
| EP | 0 661 025 B1 | 7/1995 |
| FR | 429447 | 9/1911 |
| WO | WO 94/04093 | 3/1994 |
| WO | WO 95/02375 | 1/1995 |

OTHER PUBLICATIONS

Sonex International: Brushing with the Ultima—The World's Only Dual–Frequency Ultrasonic Toothbrush, Jul. 28, 1999, published at Sonipic.com.

*Primary Examiner*—Nicholas D. Lucchesi
*Assistant Examiner*—Melba Bumgarner
(74) *Attorney, Agent, or Firm*—Dorsey & Whitney LLP

(57) ABSTRACT

A handle housing that is modular and easily assembled and disassembled for maintenance and cleaning. The handle housing has an integrally-formed orientation shape (e.g. S-shape) to keep it from tipping onto the flossing tip. The handle housing also includes the rocker arm, cam drive (together the drive train), motor, power supply and bobbin for full functionality, with linear, reciprocating motion created by the drive train for effective cleaning.

17 Claims, 10 Drawing Sheets

U.S. PATENT DOCUMENTS

| | | | |
|---|---|---|---|
| 3,760,799 A | 9/1973 | Crowson | |
| 3,809,977 A | 5/1974 | Balamuth et al. | |
| 3,831,611 A | 8/1974 | Hendricks | |
| 3,902,510 A | 9/1975 | Roth | |
| 3,903,601 A | 9/1975 | Anderson et al. | |
| 3,967,617 A | 7/1976 | Krolik | |
| 3,978,852 A | 9/1976 | Annoni | |
| 3,980,906 A | 9/1976 | Kuris et al. | |
| 4,004,344 A | 1/1977 | Gold et al. | |
| 4,005,722 A | 2/1977 | Bragg | |
| 4,008,728 A | 2/1977 | Sanchez | |
| 4,019,522 A | 4/1977 | Elbreder | |
| 4,048,723 A | 9/1977 | Thorup | |
| 4,064,883 A | 12/1977 | Oldham | |
| 4,133,339 A | 1/1979 | Naslund | |
| 4,192,035 A | 3/1980 | Kuris | |
| 4,205,664 A | 6/1980 | Baccialon | |
| 4,219,619 A | 8/1980 | Zarow | |
| 4,235,253 A | 11/1980 | Moore | |
| RE30,536 E | 3/1981 | Perdreaux, Jr. | |
| 4,289,486 A | 9/1981 | Sargeant | 433/118 |
| 4,307,740 A | 12/1981 | Florindez et al. | |
| 4,319,377 A | 3/1982 | Tarrson et al. | |
| 4,319,595 A | 3/1982 | Ulrich | |
| 4,326,547 A | 4/1982 | Verplank | |
| 4,326,548 A | 4/1982 | Wagner | |
| 4,333,197 A | 6/1982 | Kuris | |
| D265,515 S | 7/1982 | Levine | |
| 4,338,957 A | 7/1982 | Meibauer | |
| 4,347,839 A | 9/1982 | Youngclaus, Jr. | |
| 4,397,327 A | 8/1983 | Hadary | |
| D272,565 S | 2/1984 | Levine | |
| 4,434,806 A | 3/1984 | Givens | |
| 4,458,702 A | 7/1984 | Grollimund | |
| 4,505,678 A | 3/1985 | Andersson | |
| 4,576,190 A | 3/1986 | Youssef | |
| 4,577,649 A | 3/1986 | Shimenkov | |
| 4,605,025 A | 8/1986 | McSpadden | |
| 4,608,019 A | 8/1986 | Kumabe et al. | |
| 4,617,718 A | 10/1986 | Andersson | |
| 4,634,376 A | 1/1987 | Mossle et al. | |
| 4,787,847 A | 11/1988 | Martin et al. | |
| 4,791,940 A | 12/1988 | Hirshfeld et al. | |
| 4,811,445 A | 3/1989 | Lagieski et al. | |
| 4,820,153 A | 4/1989 | Romhild et al. | 433/118 |
| 4,820,154 A | 4/1989 | Romhild et al. | 433/128 |
| 4,832,063 A | 5/1989 | Smole | 132/329 |
| 4,913,133 A | 4/1990 | Tichy | |
| 4,922,936 A | 5/1990 | Buzzi et al. | 132/321 |
| 4,995,403 A | 2/1991 | Beckman et al. | 128/776 |
| 5,000,684 A | 3/1991 | Odrich | 433/125 |
| 5,002,487 A | 3/1991 | Tichy | 433/122 |
| 5,016,660 A | 5/1991 | Boggs | 132/322 |
| 5,050,625 A | 9/1991 | Siekmann | 132/323 |
| 5,067,223 A | 11/1991 | Bruno | 29/426.5 |
| 5,069,621 A | 12/1991 | Paradis | 433/147 |
| 5,071,348 A | 12/1991 | Woog | 433/118 |
| 5,094,256 A | 3/1992 | Barth | 132/322 |
| 5,100,321 A | 3/1992 | Coss et al. | 433/118 |
| 5,123,841 A | 6/1992 | Millner | 433/125 |
| 5,125,837 A | 6/1992 | Warrin et al. | 433/98 |
| 5,133,661 A | 7/1992 | Euvrard | 433/120 |
| 5,138,733 A | 8/1992 | Bock | 15/22.1 |
| 5,169,313 A | 12/1992 | Kline | 433/143 |
| 5,170,809 A | 12/1992 | Imai et al. | 132/322 |
| 5,174,314 A | 12/1992 | Charatan | 132/328 |
| 5,183,063 A | 2/1993 | Ringle et al. | 132/321 |
| 5,224,500 A | 7/1993 | Stella | 132/322 |
| 5,236,358 A | 8/1993 | Sieffert | 433/119 |
| 5,247,716 A | 9/1993 | Bock | 15/22.1 |
| 5,293,886 A | 3/1994 | Czapor | 132/329 |
| 5,323,796 A | 6/1994 | Urso | 132/322 |
| 5,369,831 A | 12/1994 | Bock | 15/22.1 |
| 5,393,229 A | 2/1995 | Ram | 433/118 |
| 5,406,965 A | 4/1995 | Levine | 132/323 |
| 5,411,041 A | 5/1995 | Ritter | 132/322 |
| 5,419,346 A | 5/1995 | Tipp | 132/329 |
| 5,419,703 A | 5/1995 | Warrin et al. | 433/216 |
| 5,482,466 A | 1/1996 | Haynes | 132/323 |
| 5,496,256 A | 3/1996 | Bock et al. | 601/2 |
| D370,125 S | 5/1996 | Craft et al. | D4/101 |
| 5,546,624 A | 8/1996 | Bock | 15/22.1 |
| 5,573,020 A | 11/1996 | Robinson | 132/322 |
| 5,579,786 A | 12/1996 | Wolk et al. | 132/322 |
| 5,606,984 A | 3/1997 | Gao | 132/325 |
| 5,618,275 A | 4/1997 | Bock | 604/290 |
| 5,700,146 A | 12/1997 | Kucar | 601/162 |
| 5,709,233 A | 1/1998 | Boland et al. | 132/322 |
| 5,718,667 A | 2/1998 | Sugimoto et al. | 601/139 |
| 5,738,575 A | 4/1998 | Bock | 433/216 |
| 5,787,908 A | 8/1998 | Robinson | 132/322 |
| 5,827,064 A | 10/1998 | Bock | 433/216 |
| 5,855,216 A | 1/1999 | Robinson | 132/322 |
| 5,896,615 A | 4/1999 | Zaksenberg | 15/167.1 |
| 5,899,693 A | 5/1999 | Himeno et al. | 433/119 |
| 5,927,300 A | 7/1999 | Boland et al. | 132/322 |
| 5,931,170 A | 8/1999 | Wu | 132/322 |
| 5,944,033 A | 8/1999 | Robinson | 132/322 |
| 6,095,811 A | 8/2000 | Stearns | 433/29 |

\* cited by examiner

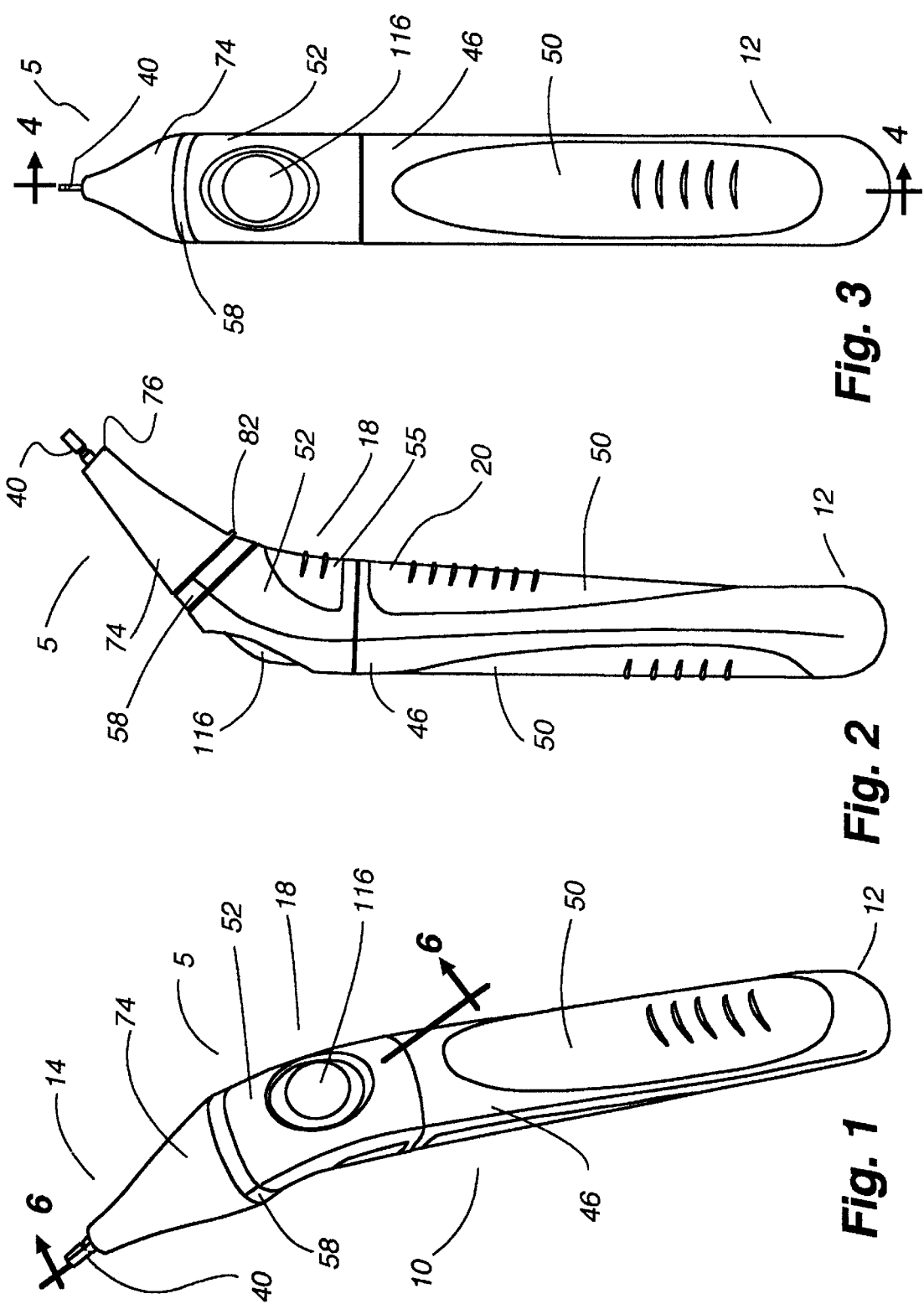

INTERPROXIMAL FLOSSER HANDLE

RELATED APPLICATIONS

This application claims the benefit of U.S. Provisional Patent Application Ser. No. 60/171,825 filed Dec. 21, 1999, from which priority is claimed.

FIELD OF THE INVENTION

This invention relates to an oral hygiene device handle and accessories, and particularly to an interproximal flosser handle having a modular component design with a removable shroud and an integrally formed resting surface.

BACKGROUND

Hand held oral hygiene devices are becoming more popular. These devices include electric toothbrushes and flossers. It is important that the handles for these devices are comfortable, allow adequate access to one's mouth, include designs that protect the devices from contamination, and are convenient to assemble.

Two substantially half-shells typically form oral hygiene handles, each representing a longitudinal half of the flosser handle. Opening this type of handle for any reason, such as replacing the battery, can result in the exposure of several components not requiring exposure, such as the motor and internal working linkages. This can lead to damage to the internal components, as well as structurally limit the style of the handle. There is a need for an oral hygiene device handle that can be opened to replace the device batteries without exposing the device internal components.

Typical designs of oral hygiene devices, when set on the counter, can tip over, causing the tip to contact the support surface and possibly contaminate the device end. There is a need for an oral hygiene device handle that includes a means for protecting the tip end of the device when the device is set on a counter.

Because of concerns with contamination, one person typically uses present oral hygiene devices. In households with multiple persons, multiple oral hygiene devices are required. There is a need for an oral hygiene device handle that includes safeguards against contamination that allow the device to be used by multiple persons within a household.

It is with these desired features, and others not stated, that the instant invention was created.

SUMMARY

The handle housing of the present invention combines several features to overcome the above-mentioned shortcomings. The handle housing is modular and easily assembled and disassembled for assembly, maintenance and cleaning. The handle housing has an integrally formed orientation shape (e.g. S-shape) to help keep it from tipping over, and thus keep the flossing tip from contacting the support surface. The shape also helps to automatically "right" the handle if it does tip over so the flossing tip does not contact the support surface.

In addition, the present invention handle housing includes means for promoting hygienic use of the device by multiple users. The present invention handle housing includes an interchangeable shroud structure near the device tip. The interchangeable structure allows different users to use different shroud structures thereby promoting hygienic use of the device.

Further, when not in use, the oral hygienic device handle is often placed on a flat surface, such as a counter top. In order to keep the end of the device that is inserted into a user's mouth from resting on the same surface and becoming contaminated, it is important to have a handle design that automatically orients the handle on the flat support surface to keep the end out of contact with the flat surface.

A preferred embodiment of the present inventive oral hygienic device handle is used in an interproximal flossing device. The interproximal flossing device handle housing also includes the rocker arm, cam drive (together the drive train), motor, power supply and bobbin for full functionality, with preferably linear, reciprocating motion created by the drive train for effective cleaning.

BRIEF DESCRIPTION OF THE DRAWINGS

FIG. 1 is a front perspective view of an interproximal flosser, according to one embodiment of the present invention;

FIG. 2 is a left side elevation view of the flosser in FIG. 1, with the right side elevation being a mirror image thereof;

FIG. 3 is a back side elevation taken along line 4—4 of the flosser in FIG. 1;

Figure 4:
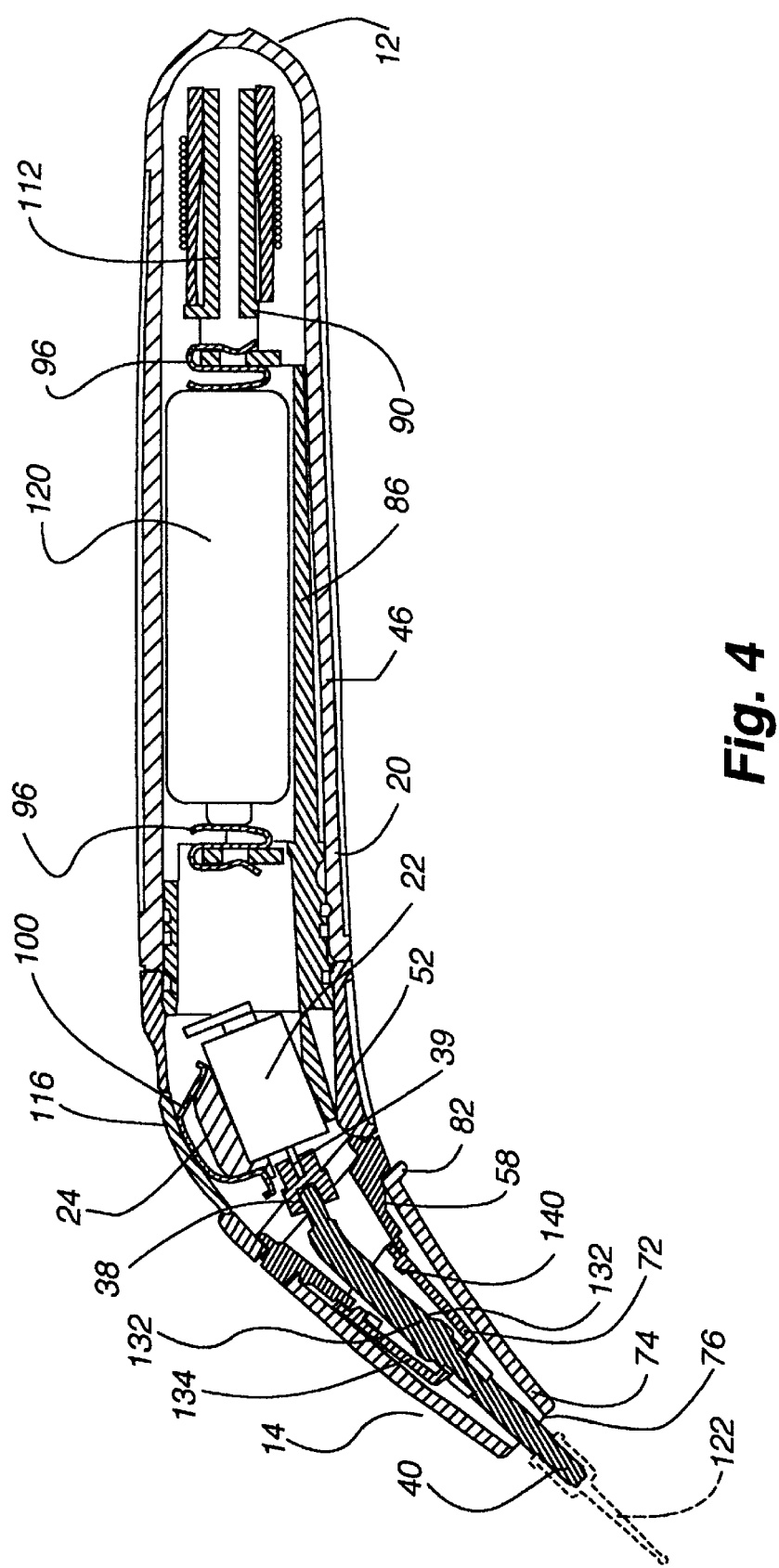
FIG. 4 is a section view of the flosser in FIG. 3.

Where one figure number is referred to below, if another figure number is listed above as disclosing similar material, it too is to be referred to.

DESCRIPTION OF THE PREFERRED EMBODIMENT

The interproximal flosser 5 of the present invention is shown in FIGS. 1–6. The interproximal flosser includes a handle housing 10 that houses a motor 22, drive mechanism 34, on-off switch 116, and power source 120. The drive mechanism has a front end 36 that extends outside of the housing to receive a flossing tip 122. The flossing tip removably engages the front end of the drive mechanism, and is inserted between a user's teeth to help clean the user's teeth and gums. The operation and function of the interproximal flossing device is described in more detail in U.S. patent application Ser. No. 09/636488, filed Aug. 10, 2000, which application is hereby incorporated by reference in its entirety.

The handle housing 10 is elongated and generally tubular in shape and generally has a base end 12 and a tip end 14. At the base end, the handle housing is generally cylindrical in shape, with relatively constant dimensions, which extends about two-thirds of the way toward the tip end. Near the tip end, the handle housing becomes roughly triangular in shape and bends to one side approximately 30–50 degrees. At the tip end, the handle housing begins reducing in dimension toward the tip end until the three general sides of the triangular shape converge to an aperture 76, through which the end 36 of the drive mechanism 34 extends for receiving the flosser tip 122. For description purposes, the side towards which the handle housing bends is the front of the flosser handle housing, and the side from which the handle housing bends away is the back or rear of the flosser handle housing.

The bend forms an angle or elbow 18, with the on-off push button switch 116 on the rear side of the housing 10, and positioned near the intersection of the bend. Preferably, the handle housing is held in the user's hand with the index finger operating the on-off switch 116. This switch position facilitates the proper holding and actuation of the switch. When the switch is depressed, the motor 22 is energized by the power source 120 (such as an AA battery 120) and actuates the drive mechanism 34. The drive mechanism includes a cam drive 38 and a rocker arm 40 for translating the rotational movement of the motor's drive shaft 39 into a linear up-and-down pivoting movement at the end of the drive mechanism extending from the handle housing. This motion drives the flossing tip 122 in a planar, reciprocating motion to clean between teeth, and between teeth and gums. When the switch 116 is not depressed, the motor 22 stops.

The handle housing 10 is made of modular components constructed of any material, such as plastic, that has the required structural characteristics. The handle housing includes a handle 46, a lower housing 52, an upper housing 58, a hygienic sleeve 72, and a shroud 74 (See FIG. 5).

Figure 5:
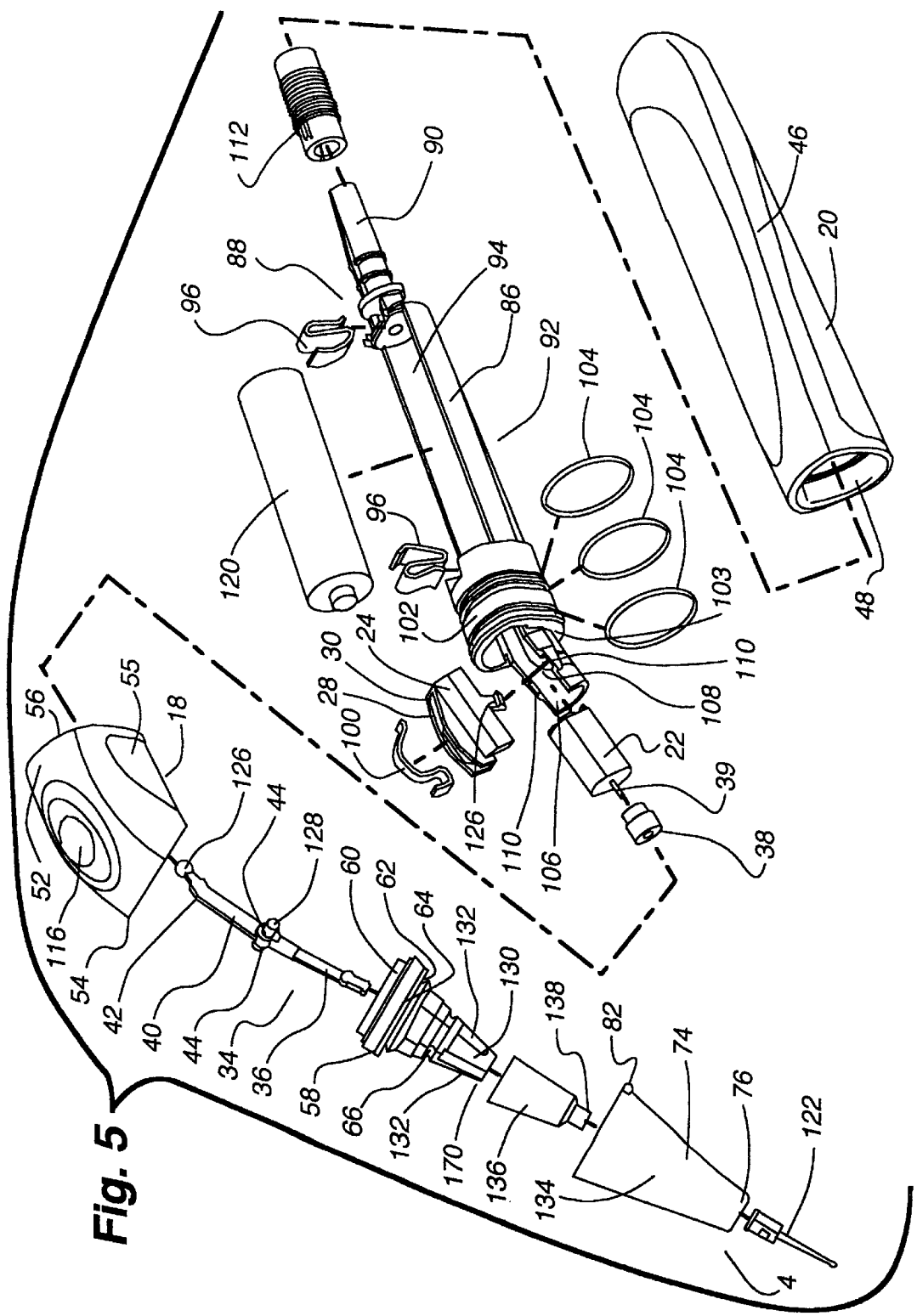
FIG. 5 is a is an exploded view of the flosser in FIG. 1.
Figure 6:
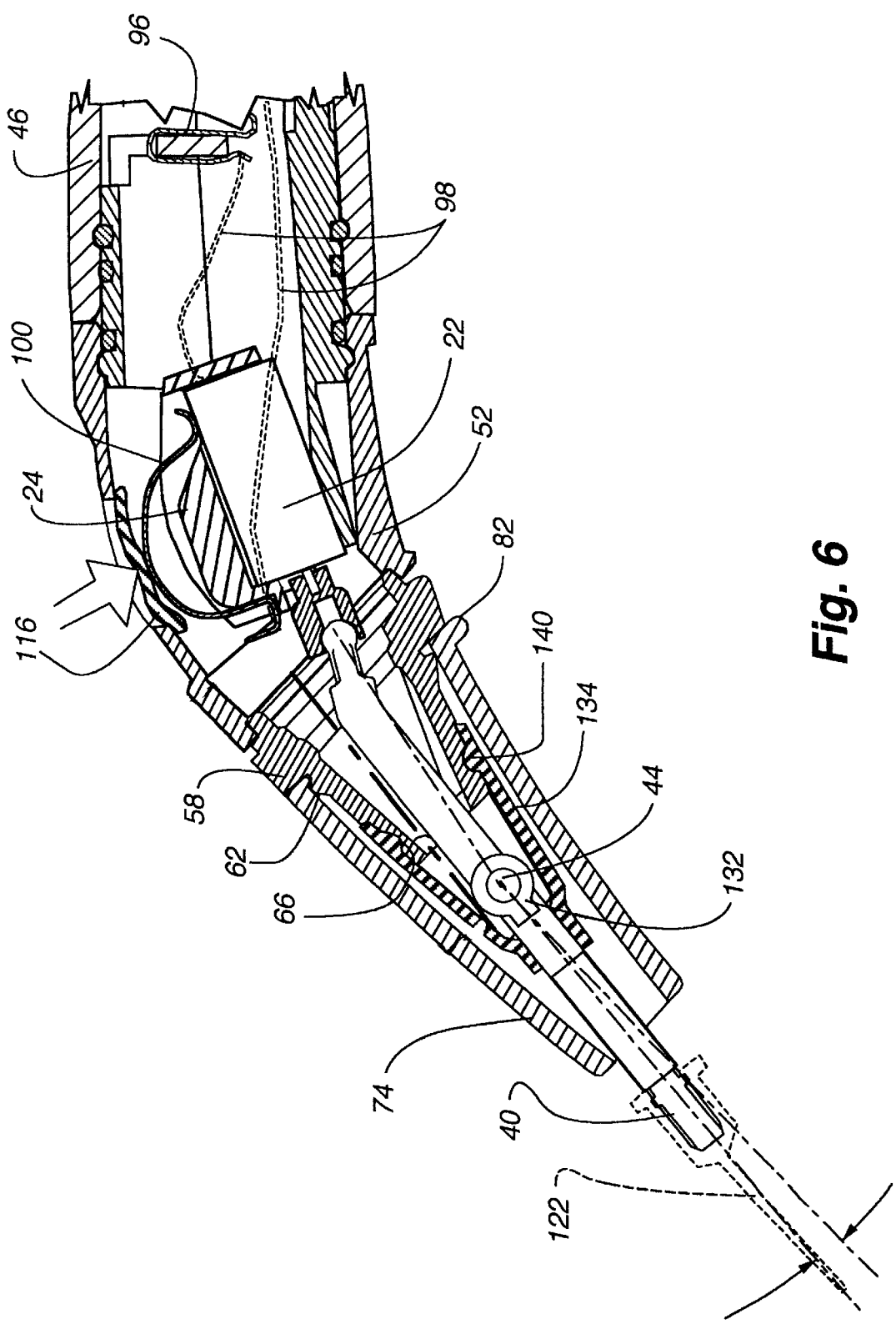
FIG. 6 is a is a section view taken along line 6—6 of the flosser in FIG. 1.
Figure 8:
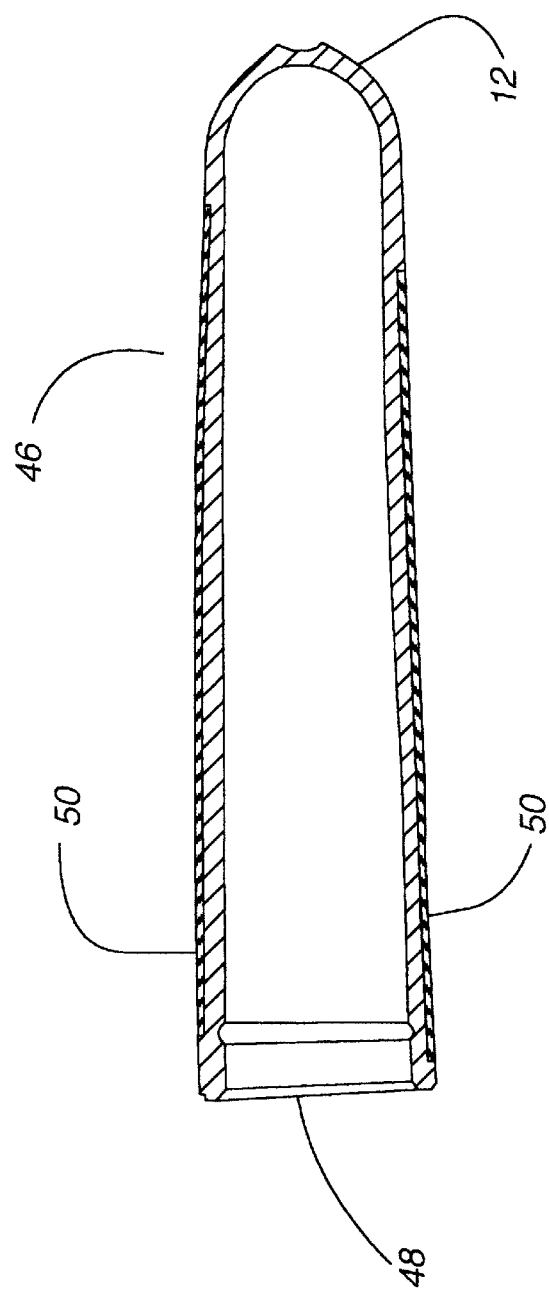
FIG. 8 is a section view taken along line 8—8 of the handle in FIG. 7.
Figure 7:
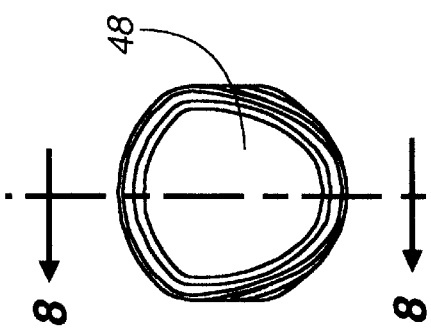
FIG. 7 is a top view of a handle portion of an interproximal flosser, according to one embodiment of the present invention.

The handle 46 is best shown in FIGS. 5, 7, and 8. The handle has a shape that changes from a generally oval or cylindrical shape at its bottom or base end 12 to a slightly triangular (preferably isosceles) configuration at its tip end 14. The oval shape has opposing relatively pointed ends. Where the section forms a triangle, the base of the triangle is the rear side of the handle, with the front side of the handle being the apex of the two longer sides of the triangle. The handle is closed at the base end 12 and open at its top end 48. The handle 46 has rubber or other grip-like material 50 (applied for instance in a co-molding process) covering its front and rear sides for the convenience of the user. The chassis 86, battery 120, and secondary bobbin 112 (used for inductive charging when the handle is inserted into an inductive charger) are the main components in the handle 46.

Figure 9:
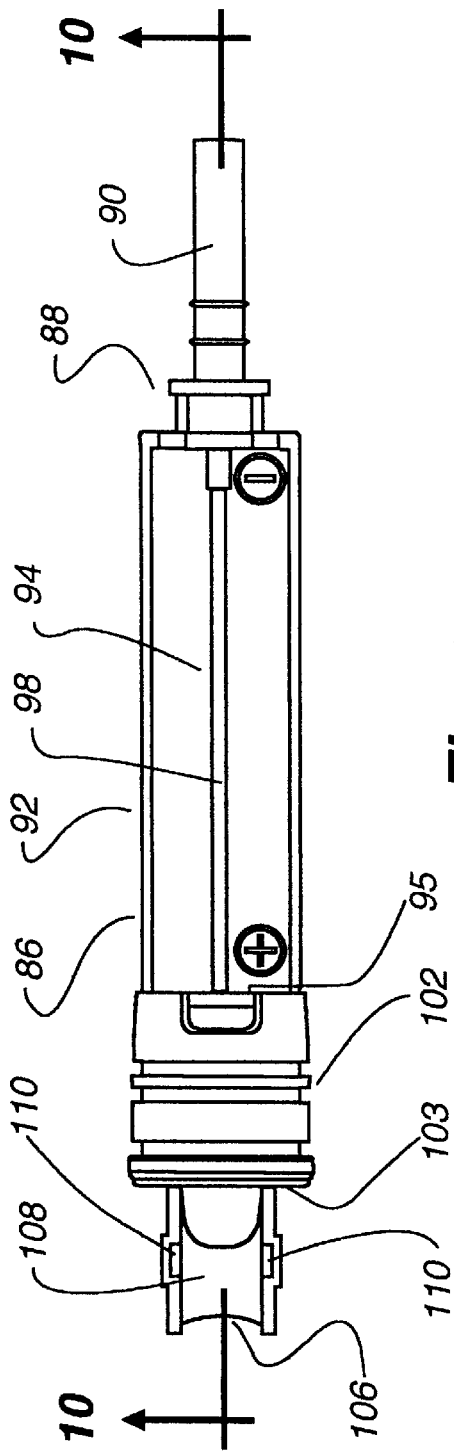
FIG. 9 is a top view of a chassis portion of an interproximal flosser, according to one embodiment of the present invention.
Figure 10:
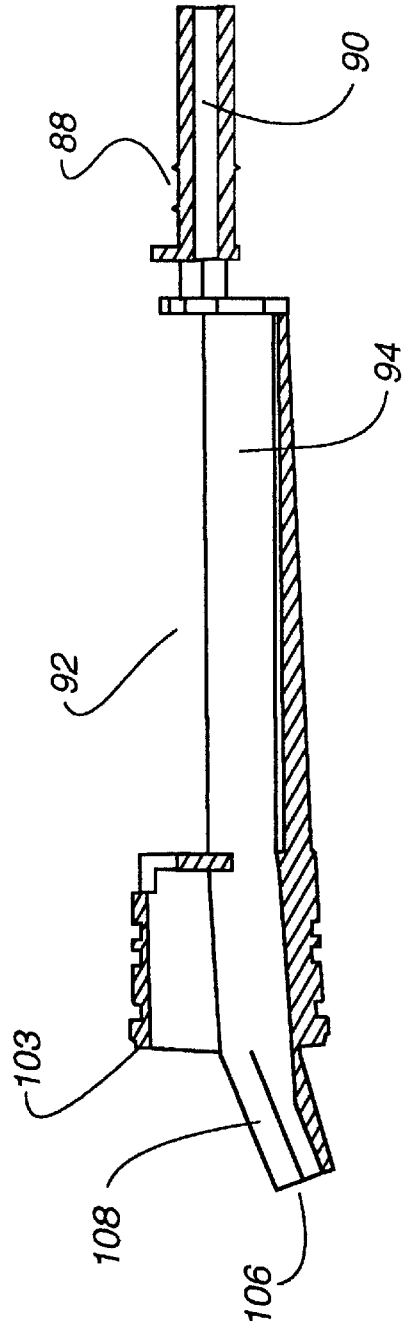
FIG. 10 is a section taken along line 10—10 of the chassis in FIG. 9.
Figure 12:
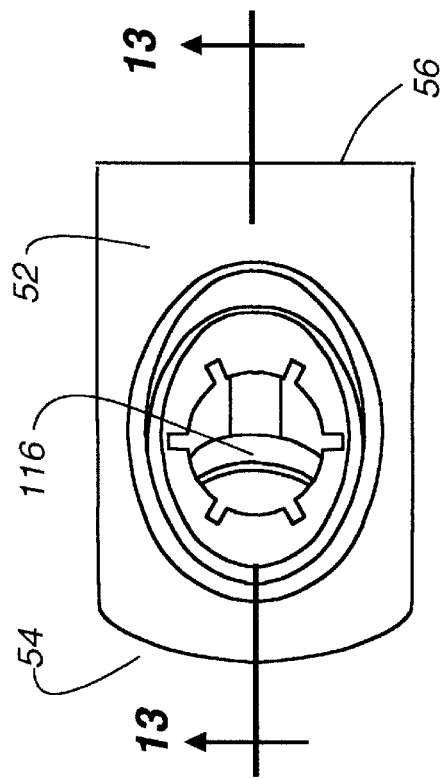
FIG. 12 is a top view of the lower housing portion in FIG. 11.
Figure 13:
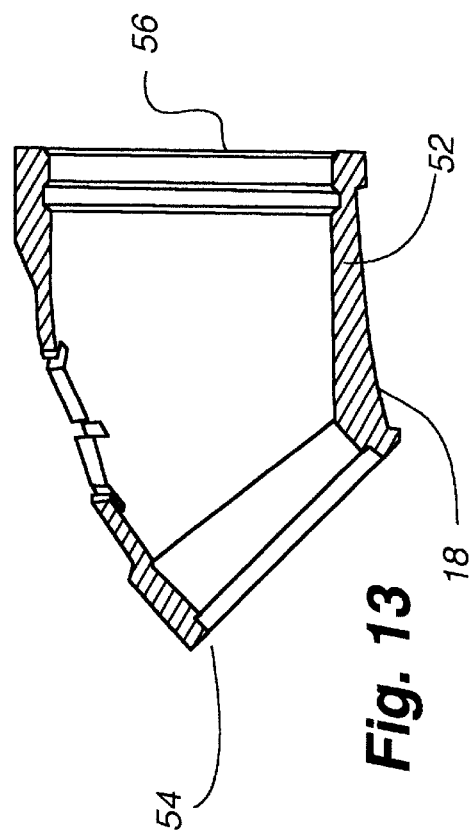
FIG. 13 is a section view taken along line 13—13 of the lower housing portion of FIG. 12.
Figure 11:
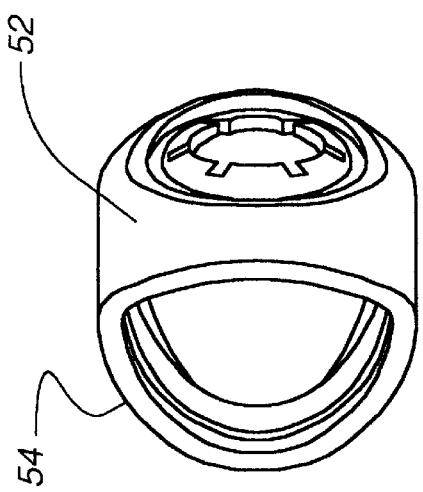
FIG. 11 is a perspective view of a lower housing portion of an interproximal flosser, according to one embodiment of the present invention.
Figure 16:
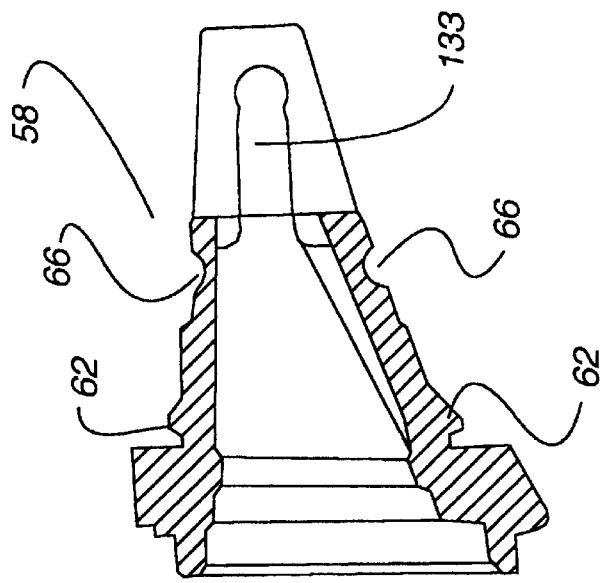
FIG. 16 is a section view taken along line 16—16 of the upper housing portion of FIG. 15.
Figure 14:
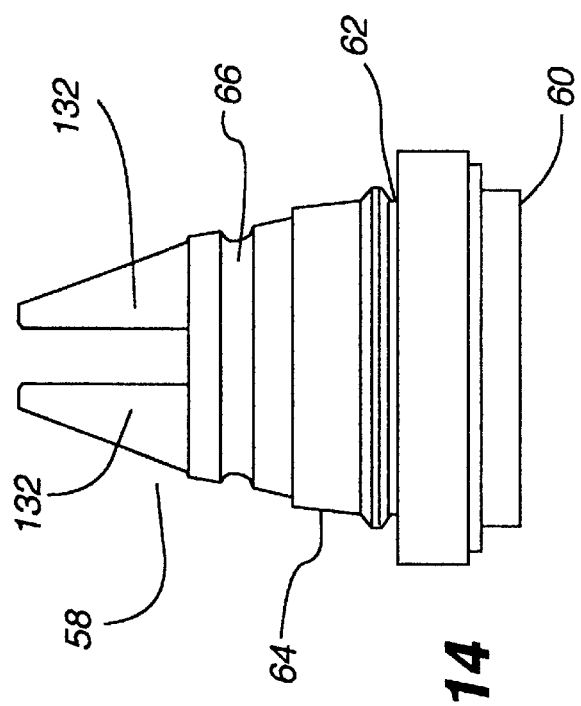
FIG. 14 is a back side view of an upper housing portion of an interproximal flosser, according to one embodiment of the present invention.
Figure 15:
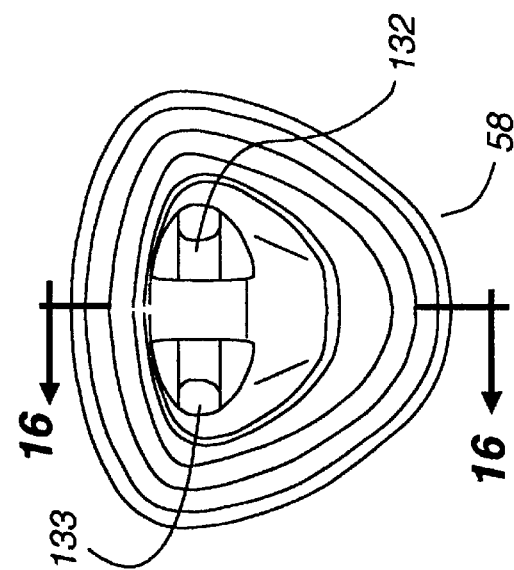
FIG. 15 is a bottom view of the upper housing portion in FIG. 14.

FIGS. 5 and 9–10 disclose the chassis 86. The chassis is configured to hold the motor 22, a battery 120, and a secondary bobbin 112 and is housed in the handle 46 and lower housing 52. The chassis is generally cylindrical and includes a bottom end portion 88, a middle portion 92, joiner portion 102, and a top end portion 106. The bottom end portion 88 of the chassis includes a cylindrical extension 90 that is configured to hold a secondary bobbin 112 for rechargeable flossers 5. The bottom end portion 88 of the chassis 86 is inserted into and through the top end 48 of the handle 46 and resides at the bottom end 12 of the handle 46. The bottom end portion of the chassis extends from the middle portion 92 of the chassis. The middle portion of the chassis includes a semi-circular channel 94 for holding a battery 120. Both ends of the channel 94 include battery contacts 96 for capturing the battery 120 power. A wire 98 connected to both contacts and running along the base of the channel transfers the battery power to a switch contact 100 (see FIGS. 4 and 6). Depressing the flosser switch 116 allows the switch contact 100 to transfer the battery power and thus energize the motor 22. In a flosser 5 that includes a secondary bobbin 112, the contact 96 at the bottom end of the channel 94 also captures the power from a base charger unit.

The top end 95 of the channel 94 is connected to the joiner portion 102 of the chassis 86. The joiner portion of the chassis has the same shape as the open top end 48 of the handle 46. The joiner portion has preferably two o-ring seals 104 formed thereon. The open top end of the handle fits over the joiner portion, and over the seals, to secure the handle thereto in a substantially water-tight manner. The o-ring seals create a tight fit sufficient to keep the handle from unintentionally disconnecting from the lower housing portion 52. The lower housing similarly slides over the top 103 of the joiner 102 to meet the top end 48 of the handle 46. Extending from the top end of the joiner portion at an angle of 0–50 degrees is the top end portion 106 of the chassis 86. The top end portion of the chassis is a semi-circular channel 108 configured to hold the motor 22. The top end portion 106 also includes two detents 110 for receiving tab portions 26 of a motor cover 24.

FIG. 5 discloses the motor cover. The motor cover includes two bottom tabs 26 (only one shown) for securing the cover to the top end portion detents 110. The top 28 of the motor cover 24 includes a groove 30 for attaching the switch contact 100. The motor cover is generally configured to fit within the lower housing 52 of the flosser 5.

Extending from the top end 28 of the motor 22 and motor cover 24 is a cam driver 38. FIG. 5 discloses one embodiment of the cam driver for use on the end of the drive shaft 39 of the electric motor 22. The cam driver 38 engages the "ball" end 126 of the rocker arm 40 and, along with the pivot structure 130, acts to convert the rotation of the electric motor to substantially linear reciprocating motion. The operation of the drive mechanism 34 is described in U.S. patent application Ser. No. 09/636488, filed Aug. 10, 2000, and is incorporated by reference above.

The handle housing 10 next includes a lower housing 52, best seen in FIGS. 5 and 11–13. The bottom end 56 of the lower housing 52 attaches to the chassis joiner 102 to be positioned in close engagement with the top, open end 48 of the handle 46. The top end 48 of the handle and the bottom end 56 of the lower housing 52 contact each other and entirely cover up the joiner 102 of the chassis 86. The lower housing 52 fits tightly over the chassis joiner 102, and is sealed therewith by an o-ring seal 104 positioned around the joiner. The joiner has the same basic shape as the lower housing to allow a allow a close fit. The lower housing defines the bend in the handle switch 116 is positioned in the back of the lower housing, and a rubber-like grip surface 55 is formed on the front face of the lower housing. The lower housing 52 covers the motor 22, motor cover 24, and cam drive 38, as well as the bottom end portion 42 of the rocker arm 40 attached to the cam drive.

The upper housing 58, as best seen in FIGS. 5 and 14–16, has a lower end 60 that has the same basic shape as the top end 54 of the lower housing 52, and snap-fits thereto. The upper housing and lower housing do not need to be taken apart after the device is assembled, so the snap-connection is relatively difficult to undo, and is basically a detent structure. It could, however, be permanently attached by any known or available means. The co-acting detent structure is formed around the bottom 60 of the upper housing 58 and around the top 54 of the lower housing 52. The upper housing exterior surface 64 also includes a groove 66 for removably engaging a tightly fitting boot 134 (described below). The upper housing 58 provides support for the pivot axis 128 of the rocker arm 40. The lower end 60 of the upper housing has substantially the same outer dimensions as the top end of the lower housing, but the upper end 70 of the upper housing 58 has a much reduced outer dimension to form the structure 130 for supporting the pivot axis 128 of the rocker arm. The structure for supporting the pivot axis of the rocker arm includes opposing triangular shaped arms 132 having key-shaped openings 133 for containing the rocker arm laterally extending tabs 44. The arms are constructed of plastic or some other relatively rigid material and are spaced apart laterally to allow for assembly and the movement of the rocker arm there between. The arms 132 allow the rocker arm tabs 44 to be snapped into the key-shaped openings 133 on the arms.

Figure 19:
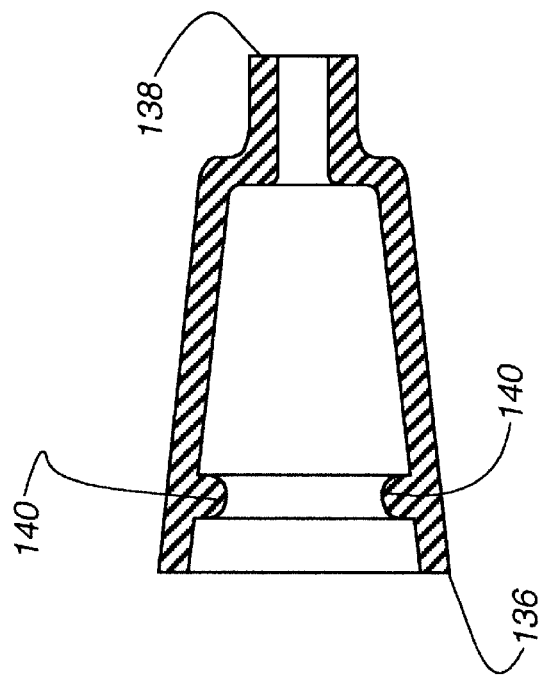
FIG. 19 is a section view taken along line 19—19 of the upper housing portion boot in FIG. 18.
Figure 18:
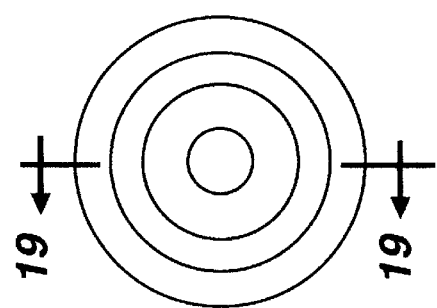
FIG. 18 is a bottom view of the upper housing portion boot in FIG. 17.
Figure 17:
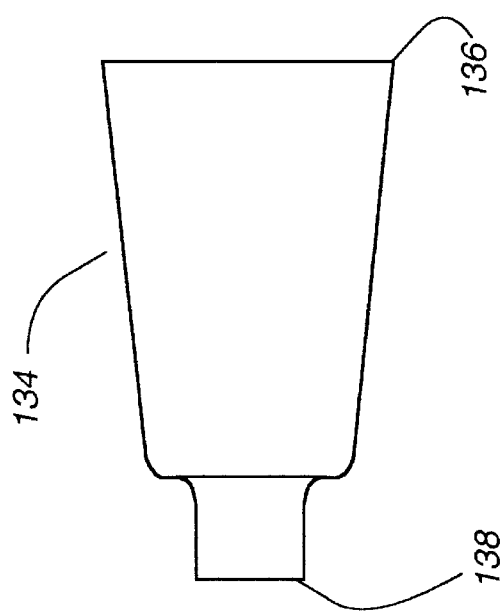
FIG. 17 is a side view of an upper housing portion boot, according to one embodiment of the present invention.
Figure 21:
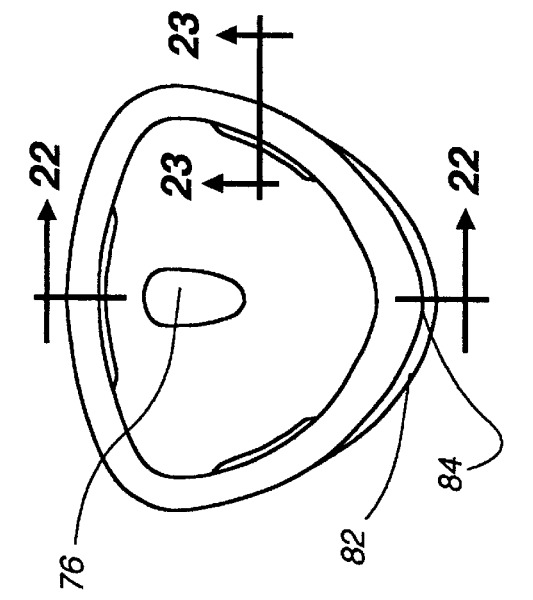
FIG. 21 is a bottom view of the tip shroud in FIG. 20.
Figure 23:
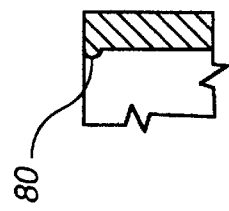
FIG. 23 is a section view taken along line 23—23 in FIG. 21.
Figure 20:
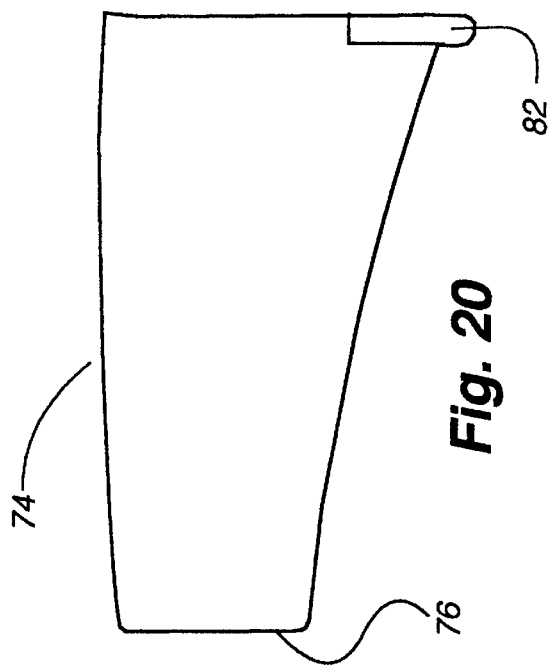
FIG. 20 is a side view of a tip shroud, according to one embodiment of the present invention.
Figure 22:
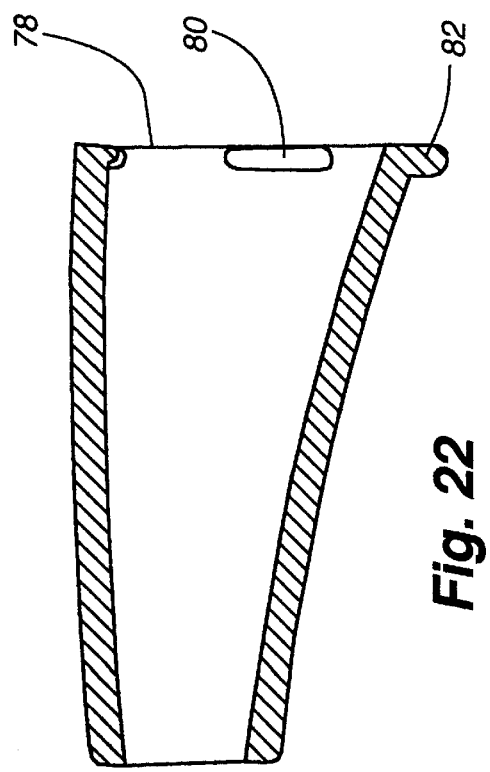
FIG. 22 is a section view taken along line 22—22 in FIG. 21.

As mentioned above, the upper end 70 of the upper housing 58 is covered by a tightly fitting boot 134 (made of a resilient material, such as rubber or plastic) that resists fluids from entering the interior of the handle housing 10 through the upper end 70 of the upper housing 58. See FIGS. 1 and 17–19. In the embodiment in FIGS. 17–19, the bottom end portion 136 is larger in diameter than the top end portion 138 to allow the boot 134 to fit over both the narrow top end 70 and wider bottom end 60 of the upper housing 58. Depending on the material used in constructing the boot 134, the boot could have end portions with equivalent diameters. A more flexible material could tightly fit around varyingly sized cross-sections of the upper housing. In the embodiment in FIGS. 17–19, the bottom end portion 136 of the boot is configured to fit around the bottom end portion 60 of the upper housing 58. The interior of the boot includes an annular raised edge portion 140 configured to releasably engage an annular seat or groove 66 formed in the upper housing exterior surface 64. This engagement helps keep the boot 134 tightly in place. The top end portion 138 of the boot is configured to fit tightly around the rocker arm 40 above the pivot point portion 128 of the arm. The boot is removable for cleaning, and helps keep the rocker arm mechanism clean and dry. A removable tip shroud 74 covers the boot and upper housing.

A tip shroud is removably attached to the upper housing 58 near the bottom end 60 of the upper housing and covers the boot 134 and upper housing. See FIGS. 5 and 20–23. The tip shroud is a relatively rigid hygienic sleeve, and covers the majority of the upper housing above the bottom end of the upper housing. The tip shroud has the same basic outer shape (substantially triangular) as the base of the upper housing, and converges to form the aperture 76 through which the end 36 of the drive mechanism 34 extends. The aperture is large enough to allow the drive mechanism to move in its reciprocating motion without interference.

The tip shroud 74 is attached by a detent mechanism with the upper housing 58. The upper housing defines a continuous groove 62 formed around its perimeter just above the bottom portion 60 of the upper housing (where the outer dimension of the upper housing decreases). The lower rim 78 of the shroud defines an inwardly-extending rib 80 on each side of the triangle. The rib 80 fits (snaps) into the groove 62 to hold the shroud in place on the upper housing. A lip 82 extends outwardly from the lower rim 78 of the shroud, at the apex 84 of the two sides of the triangular shape, and extends out beyond the edge of the lower end 60 of the upper housing. The user uses the lip to disengage the detent and push the shroud off the upper housing.

The shroud 74 can be solid, opaque, clear, colored, or transparent. It is intended for each different user of the flosser 5 to remove the prior user's shroud and replace it with their own (with an identifying color), for hygienic reasons. This, in combination with the application of a new flosser tip 122, is intended to facilitate the use of the flosser by different users while maintaining a certain level of cleanliness.

As best seen in FIG. 5, the handle housing 10 of the present invention is modular to allow for ease of manufacturing and assembly, as well as maintenance (replacing the battery 120) and cleaning. During assembly, the flosser can be easily assembled by placing the motor 22, switch 116, battery 120, and bobbin 112 on the chassis 86, dropping the chassis into the handle 46 and sliding the top end 48 of the handle over the bottom end 88 of the chassis insert 86. The lower housing 52 is then dropped over the top end 54 of the chassis and attached by sliding onto the top end 106 of the insert. The rocker arm 40 is then attached to the cam drive 38, and the upper housing 58 is then positioned over the rocker arm. The boot 134 or sleeve is then positioned over the top end 70 of the upper housing, and the hygienic shroud 74 is then attached over the top end of the upper housing and the boot.

For maintenance and cleaning, the handle 46 can be removed to replace the battery 120, and the tip shroud 74 can be removed to clean or rinse the upper housing 58 and tip 36 of the drive mechanism 34, and to be replaced for different users. This structure is very convenient for both assembly and cleaning/maintenance.

The handle housing 10 defines a curved shape along the sides. See FIGS. 1–3. The length of this intersection (considering only one in this description, the other is identical) forming the curved shape is substantially in one plane and extends from the bottom end of the handle 46, along the length of the handle, through the length of the lower housing 52, along the base end 60 of the upper housing 58, and terminates near the base of the shroud 74. Preferably, the curved shape has a dual curve (such as an "S" shape), but could include a single curve or more than two curves.) It could also include the use of three discrete, non-continuous points to define a plane.

This single-plane feature (curved, continuous, or discrete) supports the handle housing 10 on its side to keep the flossing tip 122 from contacting the surface on which the flosser 5 is sitting. In the S-shaped embodiment, this planar feature extends laterally both to the front (on the lower housing 52, upper housing 58, and shroud 74), and to the back (on the handle 46) of the handle housing to define a plane (three points define a plane). This shape feature keeps the handle housing from tipping toward its front side when set on a flat surface, and thus keeps the flossing tip 122 from contacting the surface. Also, the handle housing automatically rolls to the S-shaped side when placed in a different orientation on the flat support surface and thus "rights" itself.

This orienting curved shape surface is preferably formed integrally with the handle housing and blends nicely with the general aesthetics of the handle housing as a whole. The feature forming the continuous S-shape or discrete plane-defining feature can be, along its length, flat, or a ridge, or a combination, as the important feature is that there are three points of contact of the housing on the support surface to define a plane and be separated sufficiently front to back to support the handle housing on its side. One of these features is formed at each intersection of the front sides and the base sides of the general triangular configuration of the handle housing.

A presently preferred embodiment of the present invention and many of its improvements have been described with a degree of particularity. It should be understood that this description has been made by way of example, and that the invention is defined by the scope of the following claims.

What is claimed is:

1. An interproximal flossing device comprising:
   a handle housing;
   a motor;
   a drive train;
   a flossing tip;
   a power supply;
   said flossing tip attached to said drive train;
   said motor, drive train, and power supply positioned within said housing and operably connected to move said flossing tip; and
   wherein said handle housing defines at least one orienting surface thereon to keep said flossing tip from contacting a support surface upon which said flossing device rests;
   said orienting surface including at least three points defining a plane; and
   wherein when said handle housing is set upon the support surface with said flossing tip in contact with the support surface, said flossing device is configured to adjust to a rest position wherein said at least points of said orienting surface are in contact with the support surface and said flossing tip is elevated above the support surface.

2. A device as defined in claim 1, wherein
   said handle housing further comprises at least one side along the length of said handle housing; and
   said at least one orienting surface extends along said at least one side of said handle housing.

3. A device as defined in claim 2, wherein said at least one orienting surface is S-shaped.

4. A device as defined in claim 1, wherein
   said at least one orienting surface comprises a first orienting surface and a second orienting surface;
   said handle housing comprises a first side and a second side;
      wherein each of said first side and said second side extend along a length of said handle housing; and
      wherein said first side is opposite said second side on said handle housing; and
   wherein said first orienting surface extends along said first side of said handle housing and said second orienting surface extends along said second side of said handle housing.

5. A device as defined in claim 1, wherein said handle housing comprises:
   a handle;
   a lower housing;
   an upper housing; and
   a boot covering at least a portion of said upper housing.

6. A device as defined in claim 5, further comprising:
   a shroud for snugly fitting over at least a portion of said upper housing and all of said boot.

7. A device as defined in claim 6, wherein said shroud comprises indicia for differentiating between said shroud and at least one second shroud.

8. A device as defined in claim 7, wherein said indicia comprises color-coding of said shroud and the at least one second shroud.

9. A device as defined in claim 5, wherein said at least one orienting surface extends along said handle, said lower housing, and said upper housing.

10. A device as defined in claim 5, wherein said at least one orienting surface is bent between 30 and 50 degrees relative to the length of the handle.

11. A device as defined in claim 10, wherein said lower housing is bent between 30 and 50 degrees relative to the length of the handle; and
    said at least one orienting surface extends along said lower housing.

12. A device as defined in claim 5, wherein said boot tightly covers at least at portion of said upper housing.

13. A device as defined in claim 5, wherein said boot tightly covers at least a portion of said upper housing in a substantially water-tight manner.

14. A device as defined in claim 5, wherein said handle housing comprises a generally cylindrical shape at a first end of said handle and gradually changes to comprise a shape of three sides with a generally triangular cross-section at a second end of said handle, and through said lower housing and said upper housing.

15. A device as defined in claim 14, wherein an edge resulting from the intersection of two of said three sides of said shape with said generally triangular cross-section forms at least part of said at least one orienting surface.

16. A device as defined in claim 1, wherein said at least one orienting surface is formed in substantially a single plane.

17. A device as defined in claim 1, wherein said at least one orienting surface is curvilinear.

* * * * *